United States Patent [19]

Laine et al.

[11] Patent Number: 5,261,889
[45] Date of Patent: Nov. 16, 1993

[54] INJECTION THERAPY CATHETER

[75] Inventors: Loren A. Laine, Los Angeles, Calif.; James S. Bates, Bloomington, Ind.

[73] Assignee: Boston Scientific Corporation, Watertown, Mass.

[21] Appl. No.: 980,821

[22] Filed: Nov. 24, 1992

[51] Int. Cl.$^5$ .................... A61M 5/178; A61B 1/06
[52] U.S. Cl. ................... 604/164; 604/165; 604/272; 604/284; 128/6
[58] Field of Search ............. 128/4, 6, 8; 604/164, 604/165, 173, 181, 264, 267, 272, 284

[56] References Cited
U.S. PATENT DOCUMENTS

| | | | |
|---|---|---|---|
| 4,668,226 | 5/1987 | Owata et al. | 604/164 |
| 4,790,817 | 12/1988 | Luther | 604/164 |
| 4,808,757 | 2/1989 | Coombs | 604/272 |
| 4,857,057 | 8/1989 | Sanagi | 604/164 |
| 4,946,442 | 8/1990 | Sanagi | 604/164 |
| 5,021,044 | 6/1991 | Sharkawy | 604/264 |

OTHER PUBLICATIONS

Microvasive ® Boston Scientific Corporation, "Variject TM Sclerotherapy Needles", 1991.
Wilson-Cooke ® Medical Inc., "Gastrointestinal and Endoscopic Accessories", pp. 65-66.
David A. Gilbert et al., "Nonsurgical Management of Acute Nonvariceal Upper Gastrointestinal Bleeding", pp. 349-395.

*Primary Examiner*—John G. Weiss
*Attorney, Agent, or Firm*—Fish & Richardson

[57] ABSTRACT

A catheter for use with an endoscope includes a projectable and retractable needle for the introduction of injectable drug agents and a visual-path irrigation lumen disposed adjacent to the needle for providing irrigation fluid to a target site within body tissue. The visual-path irrigation lumen enables the user in a one-catheter procedure to displace blood or other obscuring substances such that the visual path is cleared, a target injection site endoscopically identified, the needle advanced into the tissue at the site, and the injectable agent injected into the tissue.

8 Claims, 3 Drawing Sheets

INJECTION THERAPY CATHETER

BACKGROUND OF THE INVENTION

The invention relates to injection therapy catheters which are typically employed through a working channel of an endoscope to inject fluid agents to sites within the body.

As is known in the art, such a catheter which slidably supports an extendable and retractable needle catheter, can be employed, to provide treatment to a bleeding area, for example, an ulcer in the gastrointestinal tract or the site of esophageal varices. With such treatment, drugs such as sclerosing or vasoconstrictive agents are administered to the treatment area to clot or occlude the bleeding tissue to stop bleeding or to reduce the possibility of a blood vessel bursting.

It is not uncommon for blood or other obscuring substances to obstruct the visual path at the observation port located at the distal end of the endoscope. In such circumstances, the physician's ability to accurately position the catheter is hindered. One approach for clearing the worksite is to remove the drug administering catheter and provide a separate irrigation catheter to wash away the obscuring material. The drug administering catheter is then reintroduced to the target site.

SUMMARY OF THE INVENTION

In general, in one aspect, the invention features an injection therapy catheter for endoscopically guided introduction of injectable fluid agents such as blood coagulants and vasoconstrictors into selected sites within a body and which includes a special provision for physician-activated irrigation to clear the visual path with the injection catheter still in place. The injection catheter is sized for passage through a working channel of an endoscope and is constructed to be maneuvered therethrough to a site at which, for instance, bleeding may occur. The injection catheter includes a needle lumen terminating at a distal end of the catheter in a distal needle port and an extendable and retractable needle catheter slidably disposed in the needle lumen and terminating distally in a tissue-penetrable hollow needle. The needle is projectable and retractable relative to the needle port by an actuating motion applied to a proximal end of the injection catheter with the needle being adapted for penetration of tissue at a location determined by visual examination by the physician through the endoscope for injection of the injectable fluid agents. The injection catheter includes a visual-path irrigation lumen, the distal outlet thereof being located adjacent the needle port and directed to introduce clear irrigation fluid in a flow that enhances the visual path from the associated endoscope to tissue near to which the distal end of the injection therapy catheter has been advanced, to displace fluid containing blood or other obscuring substance from a potential target site at the tissue. Thus the physician is enabled in a one-catheter procedure to clarify the visual path, endoscopically identify a target injection site, advance the needle into the tissue at the site and inject the injectable agent.

Embodiments of the invention include the following features. The visual-path irrigation lumen and its distal outlet are elongated in transverse cross-section to project a substantial, somewhat flattened stream of irrigation fluid for clarifying the visual path to both sides of a center plane projected through the center of the distal outlet of the irrigation lumen and the center of the needle port. The visual-path irrigation lumen has a substantially constant flow cross-section along the length of the catheter and the outer surface of the distal portion of the catheter tapers to a smaller size toward the distal end for enhancing entry and the physician's field of view. The irrigation lumen is disposed below the needle port, and the upper outside distal corner of the catheter is locally chamfered to enhance visualization by the physician. The needle catheter is connected to a source of injectable agent capable of reducing bleeding at the selected site, the catheter adapted to introduce the injectable agent into the selected site to at least temporarily slow or stop bleeding at the site. The needle catheter includes a proximal actuation device having limit means to limit the extent of projection of the needle to a predetermined extended position and detent means, effective with the needle in the extended position, to provide a selected degree of resistance to retraction of the needle, to enable the needle to be pushed against and penetrate relatively hard tissue. The injection catheter further includes a second limit means adapted to prevent retraction of the needle catheter beyond a selected distance. The transverse cross-section of visual-path irrigation lumen narrows toward the distal end to provide a nozzle effect to the irrigation fluid at the distal outlet of the irrigation lumen.

DESCRIPTION OF THE PREFERRED EMBODIMENT(S)

Figure 1:
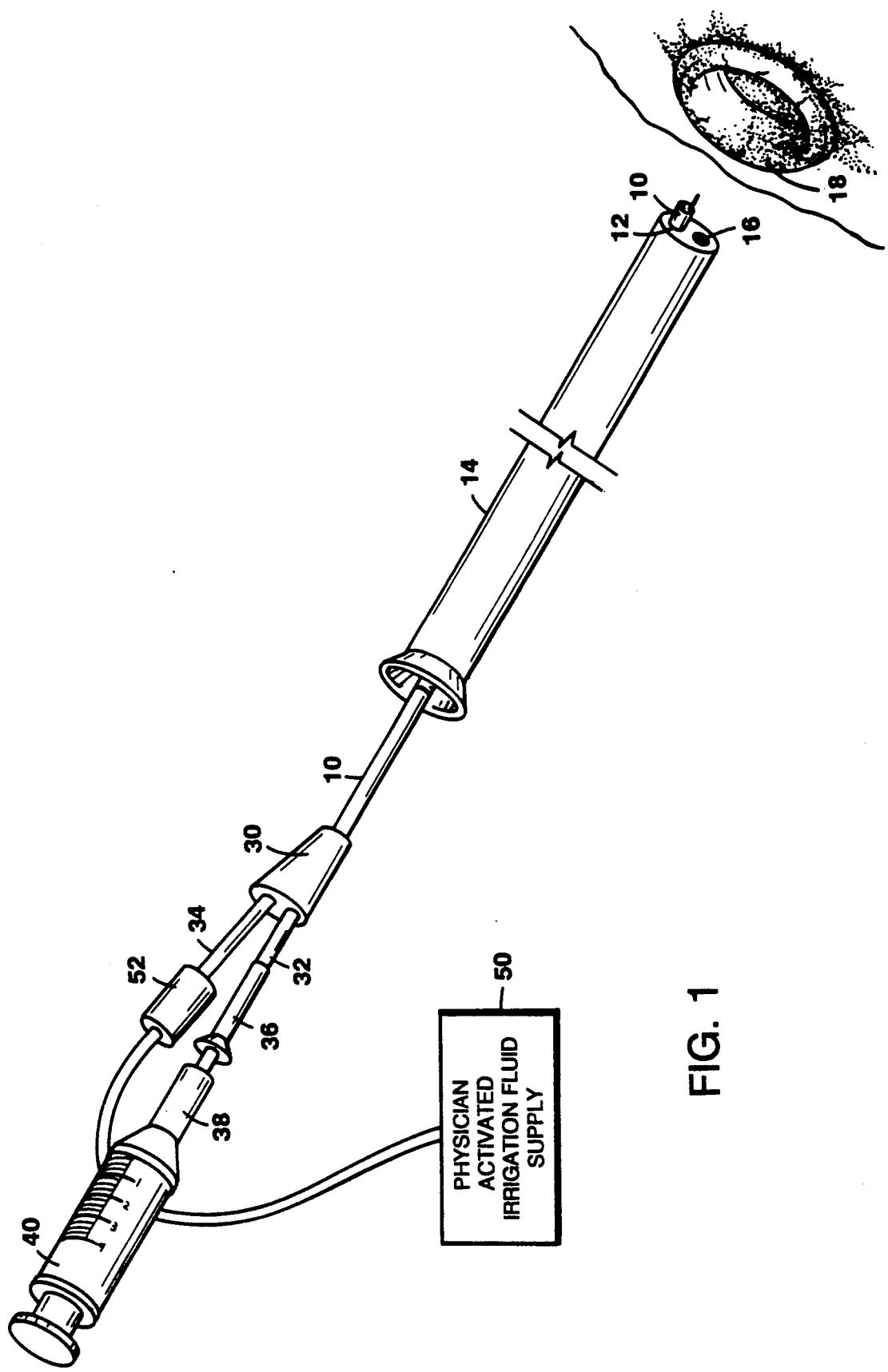
FIG. 1 is a diagrammatic view of a catheter of the invention disposed within an endoscope.
Figure 2:
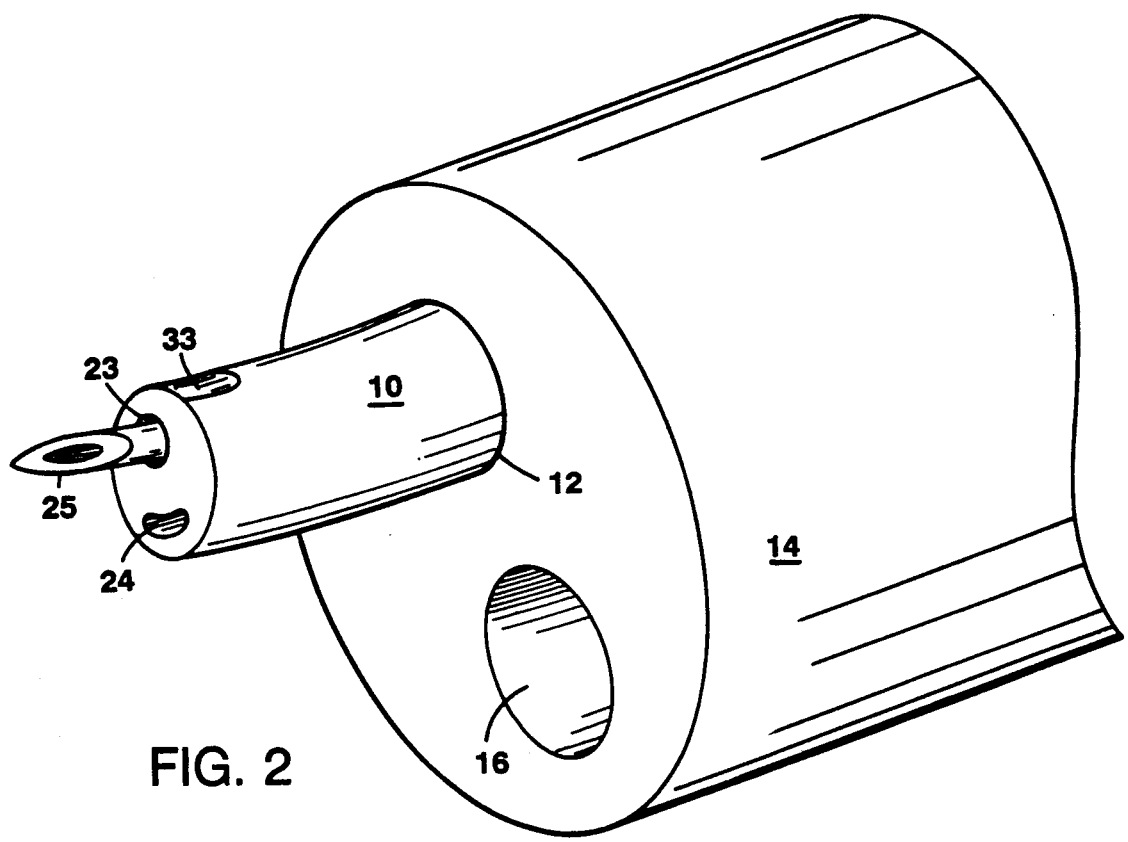
FIG. 2 is a perspective view of the catheter and endoscope in the region of 2—2 of FIG. 1.

Referring to FIGS. 1 and 2, an injection therapy catheter 10, pushed through a working channel 12 of an endoscope 14, is placed within the human body at a location proximate to an ulcerated lining 18 of the stomach. The endoscope 14 includes at a distal end an observation port 16 to enable the physician to visually examine the site of the ulcerated lining.

Figure 3:
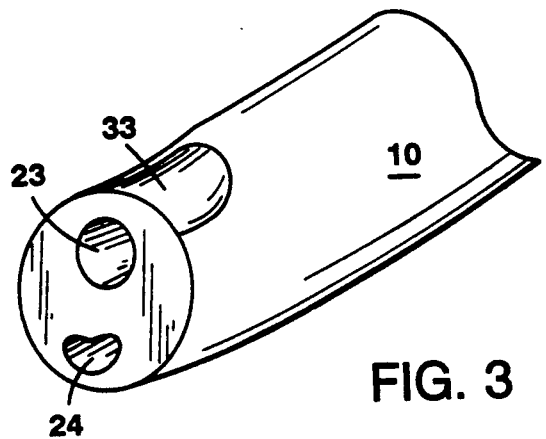
FIG. 3 is a perspective view of the catheter with the metal needle retracted.
Figure 4:
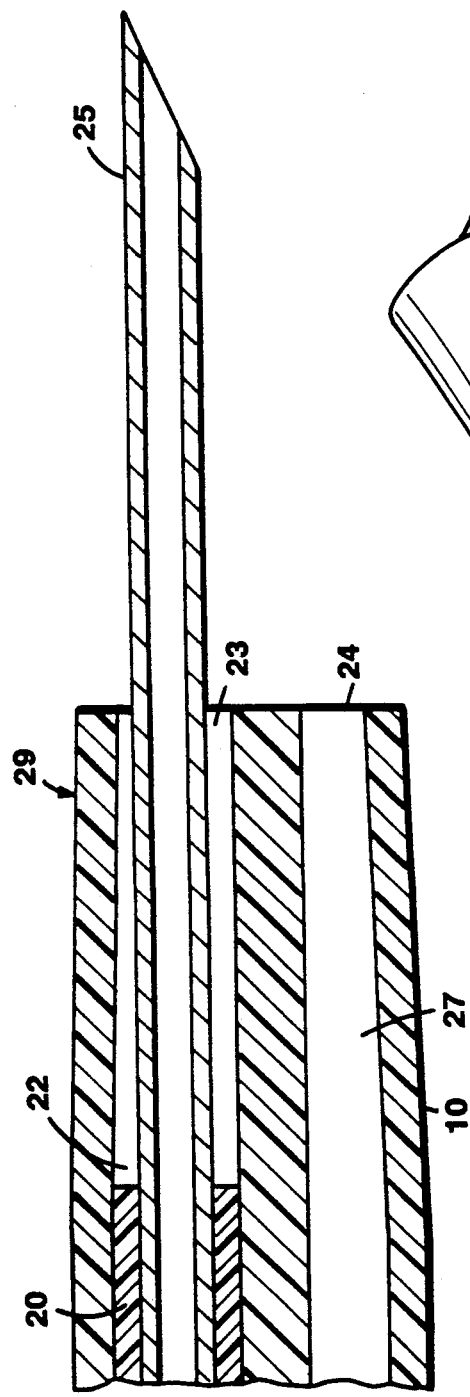
FIG. 4 is a cross-sectional side view of the distal end portion of the catheter.

Referring to FIGS. 2-4, injection therapy catheter 10 has an outer diameter of about 2.8 mm and includes a needle lumen 22 with a hollow inner sheath 20 slidably disposed therein. The inner sheath has an outer diameter of about 0.054 inches and an inner diameter of about 0.023 inches. Catheter 10 and inner sheath 20 are fabricated from plastic materials and are relatively flexible. The distal portion 29 of catheter 10 is tapered to a smaller size in order to facilitate insertion within the tissue and to also enhance the physician's field of view. Alternatively, an upper outside distal corner 33 may be chamfered to provide an enhanced field of view (See FIGS. 2, 3, and 5).

The hollow inner sheath 20 has at a distal end a metal needle 25 that is firmly fitted within the inner diameter of the inner sheath 20. Needle 25 and its sheath are slidably disposed within lumen 22 and act as an extendable and retractable needle catheter. The needle is thus projectable and retractable from a needle port 23 at the distal end of needle lumen 22 of the injection therapy catheter 10. Needle 25 is approximately one inch long, is fully retractable (See FIG. 3) within injection therapy catheter 10 for maneuvering through the endoscope 14 and can be extended to position its tip about 6 mm from the needle port 23 for injection therapy. The tip of needle 25 is pointed to facilitate penetration into the tissue of the target site and is hollow to permit the introduction of a vasoconstrictor, such as epinephrine, to constrict the tissue to thereby reduce blood flow at the ulcerated site. In operation, the physician having found the area to be treated, projects needle 25 into the tissue of the ulcer bed and injects the vasoconstrictor.

It is appreciated that injection therapy catheter 10 may be used in the treatment of other bodily disorders. For example, in another preferred embodiment, injection therapy catheter 10 may be used in the treatment of esophageal varices, a condition where blood vessels of the esophagus are enlarged and may potentially burst. For such a condition, the injection therapy catheter 10 is properly positioned near the enlarged varix, needle 25 is projected into the tissue and a coagulant, such as sodium morrhuate is injected into the tissue to cause occlusion of the varix.

Injection therapy catheter 10 includes a visual-path irrigation lumen 27 extending through the catheter and terminating at an irrigation port 24 disposed at the distal end of the catheter at a location adjacent to and below the needle port 23. Fluids containing blood or other obscuring substances hinder the physician in viewing and identifying the target site. When this condition occurs, the physician employs the irrigation lumen 27 to introduce clear irrigation fluid to clear the visual path of the observation port 16 of endoscope 14 while the injection catheter remains in place.

The irrigation lumen 27, extruded as part of the body of catheter 10, provides an elongated, substantially constant flow cross-section for projecting a substantial, somewhat flattened stream of the irrigation fluid to the target site. In this way, the visual path on both sides of a center plane projected through the center of the distal end of the irrigation lumen 27 and the center of needle port 23 is clarified. Irrigation lumen 27 in a preferred embodiment may have a slightly reduced cross-section at the distal portion 29 of catheter 10 due to its tapered geometry. Such a narrowing of the irrigation lumen 27 provides a beneficial nozzle effect to the stream of fluid leaving the lumen 27.

Figure 5:
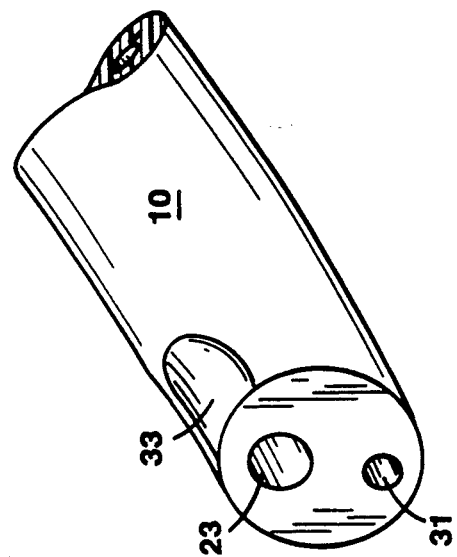
FIG. 5 is a perspective view, similar to FIG. 3, of another embodiment of the catheter of the present invention.

It is appreciated that the visual-path irrigation lumen may have a variety of cross-sectional geometries. For example, as shown in FIG. 5, injection therapy catheter 10 includes a visual-path irrigation lumen 31 having a circular cross-section.

Referring again to FIG. 1, catheter 10 has at its proximal end a molded bifurcation 30 with a pair of tubes 32, 34 extending from a proximal end for supporting visual path irrigation and injection therapy drug introduction conduits. Inner sheath 20 is disposed through tube 32 and a handle 36 to be connected to an injection lumen hub 38. A syringe 40 is coupled to the end of injection lumen hub 38 to introduce the sclerotic or other drug agent through inner sheath 20 and to the treatment site via needle 25.

Figure 6:
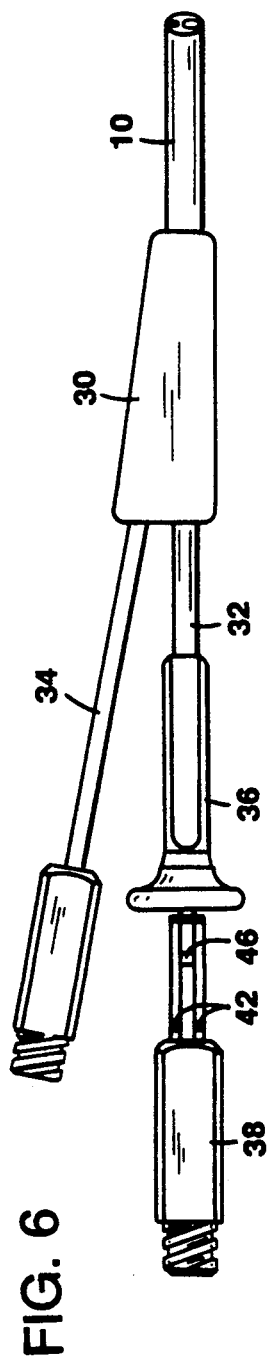
FIG. 6 is a side view of the proximal portion of the catheter.

As shown in FIG. 6, handle 36 is a Snap-Grip ™ handle, a product of Microvasive, Boston Scientific Corporation, Watertown, Mass. which cooperates with ramped members 42 on the outer surface of injection lumen hub 38 to provide a detent for limiting the extent of projection of needle 25 to a predetermined position. Needle 25 when locked into place in this way is prevented from retracting into catheter 10 and is afforded a sufficient degree of resistance to facilitate penetration into the relatively hard tissue. To operate the locking feature, the Snap-Grip ™ handle is held with one hand and injection lumen hub 38 is pushed into handle 36 with the other hand until a lipped portion on an inner surface of handle 36 engages ramped members 42 of injection lumen hub 38.

As mentioned above, distal portion 29 of catheter 10 is tapered such that the inner diameter of needle lumen 22 decreases as it progresses toward needle port 23 to the extent that inner sheath 22 is not permitted to travel beyond the taper (FIG. 4). With this arrangement, the taper serves as a distal stop to limit the extended position of needle tip 25. Chamfer 33, described earlier may similarly provide such limiting means.

A second detent, includes projecting members 46 disposed on the outer surface of injection lumen 38 to prevent retraction of the catheter 10 beyond a selected distance. Projecting members 46 are positioned at a region disposed within handle 36 such that when needle tip 36 is desired to be retracted, ramped members 42 are disengaged and injection lumen 38 pulled away from handle 36. However, projecting members 46 are sized to interfere with the inner surface of handle 36 prevent the injection lumen from fully withdrawing from the handle and to maintain catheter 10 within the selected travel distance. It should be noted that in FIG. 6, injection lumen 38 is shown fully withdrawn from handle 36 in order to better present the features of injection lumen 38 which are normally hidden.

Second tube 34 is directly connected to visual path irrigation lumen 27 at a distal end within bifurcation 30 and is connected to a physician-activated irrigation fluid supply 50 via an irrigation lumen hub 52. Irrigation fluid supply includes a single action pumping system for providing controlled flow of the irrigation fluid to the treatment site when desired by the physician for clearing the visual path.

Thus, the concept for directly irrigating at a site of injection therapy treatment is provided for enhancing the physician's view and clarity of the area to be treated.

Other embodiments are within the following claims.

What is claimed is:

1. An injection therapy catheter for endoscopically guided introduction of injectable fluid agents such as blood coagulants and vasoconstrictors into selected sites within a body, said injection catheter sized for passage through a working channel of an endoscope and constructed to be maneuvered therethrough to a site at which, for instance, bleeding may occur, said injection catheter including a needle lumen terminating at a distal end of said catheter in a distal needle port, an extendable and retractable needle catheter slidably disposed in said needle lumen and terminating distally in a tissue-penetrable hollow needle, said needle projectable and retractable relative to said needle port by actuating motion applied to a proximal end of the injection catheter, said needle adapted for penetration of tissue at a location determined by visual examination by the physician through the endoscope for injection of said injectable fluid agents, said injection catheter including a visual-path irrigation lumen, the distal outlet thereof being located adjacent the needle port and directed to introduce clear irrigation fluid in a flow that enhances the visual path from the associated endoscope to tissue near to which the distal end of said injection therapy catheter has been advanced, thereby to displace fluid containing blood or other obscuring substance from a potential target site at said tissue and enable the physician in a one-catheter procedure to clarify the visual path, endoscopically identify a target injection site, advance said needle into the tissue at said site and inject said injectable agent.

2. The injection therapy catheter of claim 1 wherein said visual-path irrigation lumen and its distal outlet are elongated in transverse cross-section to project a substantial somewhat flattened stream of irrigation fluid for clarifying the visual path to both sides of a center plane projected through the center of the distal outlet of said irrigation lumen and the center of said needle port.

3. The injection therapy catheter of claim 1 or 2 wherein said visual-path irrigation lumen has a substantially constant flow cross-section along the length of said catheter and the outer surface of the distal portion of said catheter tapers to a smaller size toward the distal end for enhancing entry and the physician's field of view.

4. The injection catheter of claim 1 or 2 wherein the outlet of said visual-path irrigation lumen is disposed below said needle port, and the upper outside distal corner of said catheter is locally chamfered to enhance visualization by the physician.

5. The injection catheter of claim 1 or 2 wherein said needle catheter is connected to a source of injectable agent capable of reducing bleeding at the selected site, said catheter adapted to introduce said injectable agent into the selected site to at least temporarily slow or stop bleeding at said site.

6. The injection catheter of claim 1 or 2 wherein said needle catheter includes a proximal actuation device having limit means to limit the extent of projection of said needle to a predetermined extended position and detent means, effective with the needle in said extended position to provide a selected degree of resistance to retraction of said needle, to enable said needle to be pushed against and penetrate relatively hard tissue.

7. The injection catheter of claim 6 including a second limit means adapted to prevent retraction of said needle catheter beyond a selected distance.

8. The injection catheter of claim 3 wherein a transverse cross-section of visual-path irrigation lumen narrows toward the distal end to provide a nozzle effect to the irrigation fluid at the distal outlet of the irrigation lumen.

* * * * *